(12) United States Patent  
Miyazaki et al.

(10) Patent No.: US 9,156,779 B2  
(45) Date of Patent: Oct. 13, 2015

(54) METHOD FOR PRODUCING TRIFLUOROMETHANESULFONIC ANHYDRIDE

(71) Applicant: Central Glass Company, Limited, Ube-shi, Yamaguchi (JP)

(72) Inventors: Tatsuo Miyazaki, Saitama (JP); Hiromi Kawamoto, Sanyoonoda (JP); Hiroshi Ono, Ube (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

(21) Appl. No.: 14/361,469

(22) PCT Filed: Oct. 10, 2012

(86) PCT No.: PCT/JP2012/076153

§ 371 (c)(1),
(2) Date: May 29, 2014

(87) PCT Pub. No.: WO2013/080676

PCT Pub. Date: Jun. 6, 2013

(65) Prior Publication Data

US 2014/0323762 A1    Oct. 30, 2014

(30) Foreign Application Priority Data

Nov. 30, 2011  (JP) .................................. 2011-262371

(51) Int. Cl.
*C07C 303/00* (2006.01)

(52) U.S. Cl.
CPC .................................... *C07C 303/00* (2013.01)

(58) Field of Classification Search
CPC ............................ C07C 303/00; C07C 309/00
USPC ........................................................ 562/872
See application file for complete search history.

(56) References Cited

U.S. PATENT DOCUMENTS

| 5,004,829 | A | 4/1991 | Aramaki et al. |
|---|---|---|---|
| 5,808,149 | A | 9/1998 | Nakamura et al. |
| 6,710,141 | B1 | 3/2004 | Heide et al. |
| 8,716,468 | B2 | 5/2014 | Bogaert |
| 2009/0118543 | A1 | 5/2009 | Yatsuyanagi et al. |
| 2010/0240884 | A1 | 9/2010 | Bogaert |

FOREIGN PATENT DOCUMENTS

| JP | 2-268148 | A | 11/1990 |
|---|---|---|---|
| JP | 9-227498 | A | 9/1997 |
| JP | 10-114734 | A | 5/1998 |
| JP | 2000-191631 | A | 7/2000 |
| JP | 2003-514961 | A | 4/2003 |
| JP | 2007-145815 | A | 6/2007 |
| JP | 2007-297359 | A | 11/2007 |
| JP | 2009-540068 | A | 11/2009 |
| RU | 2 282 620 | C1 | 8/2006 |

OTHER PUBLICATIONS

International Search Report (PCT/ISA/210) dated Jan. 15, 2013, with English translation (Five (5) pages).

*Primary Examiner* — Yong Chu
*Assistant Examiner* — Ana Z Muresan
(74) *Attorney, Agent, or Firm* — Crowell & Moring LLP

(57) ABSTRACT

Disclosed is a method for producing a Trifluoromethanesulfonic anhydride, which is characterized by that a reaction is conducted while kneading a Trifluoromethanesulfonic acid and diphosphorus pentoxide at a temperature that is 40° C. or higher and is lower than 100° C. by using a kneader-type reactor having a maximum power of 1.0 kW or greater per an actual capacity of 100 L and equipped with at least two-shaft blades, that the Trifluoromethanesulfonic anhydride to be generated is discharged, and that, while the residue in the reactor after the discharge is kneaded at a temperature that is 100° C. or higher and is lower than 140° C., the unreacted Trifluoromethanesulfonic acid is discharged, recovered and reused as the raw material. It is possible by this method to obtain a Trifluoromethanesulfonic anhydride with a high yield.

12 Claims, No Drawings

METHOD FOR PRODUCING TRIFLUOROMETHANESULFONIC ANHYDRIDE

TECHNICAL FIELD

The present invention relates to a method for producing fluoroalkanesulfonic anhydrides, which are useful as catalysts or raw materials for synthesizing medicines, organic compounds, etc., by reacting fluoroalkanesulfonic acids with diphosphorus pentoxide.

BACKGROUND OF THE INVENTION

Hitherto, as a method for producing fluoroalkanesulfonic anhydrides, when citing as an example a method for producing trifluoromethanesulfonic anhydride $((CF_3SO_2)_2O)$, there has been known a method for producing the same by a dehydration condensation reaction by using trifluoromethanesulfonic acid $(CF_3SO_3H)$ as a starting raw material and by adding diphosphorus pentoxide $(P_2O_5)$ to trifluoromethanesulfonic acid as shown in the following reaction formula 1. In the case of using this method, the trifluoromethanesulfonic anhydride formed is recovered by evaporation by heating.

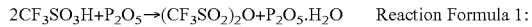
Reaction Formula 1: $2CF_3SO_3H + P_2O_5 \rightarrow (CF_3SO_2)_2O + P_2O_5 \cdot H_2O$ In the present method, however, metaphosphoric acid $(P_2O_5 \cdot H_2O)$ produced as a by-product by the dehydration condensation reaction of trifluoromethanesulfonic acid is glassy to have a very high viscosity. Thus, stirring becomes impossible in the middle of the reaction by using one-shaft blades, stirring-type reactor that is generally used for mixing and stirring high viscosity materials. Therefore, the reaction does not proceed, and it also becomes impossible to recover the trifluoromethanesulfonic anhydride formed. Thus, yield of trifluoromethanesulfonic anhydride becomes 60% or lower at the maximum, based on trifluoromethanesulfonic acid.

Thus, there is known a method (Patent Publication 1) for recovering the unreacted trifluoromethanesulfonic acid by conducting again a distillation under reduced pressure after having a condition that stirring of the reactor has been made possible by dissolving metaphosphoric acid by adding water or phosphoric acid to this glassy reaction residue.

In this method, however, it is necessary to stop the reaction once and gradually add water or phosphoric acid to avoid a rapid temperature increase by the reaction heat. Furthermore, it is not possible to conduct stirring either until it dissolves. Therefore, it is necessary to wait for long hours until metaphosphoric is completely dissolved in the added water or phosphoric acid. Viewing it from the industrial viewpoint, it is difficult to consider that the method is necessarily a process superior in productivity.

On the other hand, in order to correct the low yield by solidification of metaphosphoric acid, it is known that solidification by metaphosphoric acid during the reaction can be suppressed, by a method (Patent Publications 2 and 3) in which trifluoromethanesulfonic acid and diphosphorus pentoxide are reacted in a fluorine-series solvent, a method (Patent Publication 4) in which trifluoromethanesulfonic acid is used in an excessive amount relative to diphosphorus pentoxide, and the like. However, in order to obtain a viscosity at the level of being able to maintain at least stirring during the reaction, it is necessary to use a large amount of solvent or a large amount of the raw material that is not consumed by the reaction. Therefore, viewing from the industrial viewpoint, it is difficult to consider that the method is necessarily a process superior in productivity.

In contrast with the above-mentioned method, as a method for producing a fluoroalkylsulfonic anhydride with a high yield, there is known a method (Patent Publication 5) in which kneading is compulsorily conducted even under a condition of solidification by metaphosphoric acid to continue the reaction, by reacting the fluoroalkylsulfonic acid with diphosphorus pentoxide by using a kneader-type reactor equipped with two-shaft blades.

Furthermore, it is known that kneader-type reactors are used in the method for producing polysaccharides (Patent Publication 6) and the method for producing geleous polymerizates (Patent Publication 7).

PRIOR ART PUBLICATIONS

Patent Publications

Patent Publication 1: Japanese Patent Application Publication Heisei 2-268148.
Patent Publication 2: Japanese Patent Application Publication Heisei 09-227498.
Patent Publication 3: Japanese Patent Application Publication Heisei 10-114734.
Patent Publication 4: Japanese Patent Application Publication 2007-145815.
Patent Publication 5: Japanese Patent Application Publication 2007-297359.
Patent Publication 6: Japanese Patent Application Publication 2009-540068.
Patent Publication 7: Japanese Patent Application Publication 2003-514961.

SUMMARY OF THE INVENTION

The conventional method by reacting a fluoroalkylsulfonic acid with diphosphorus pentoxide using a kneader-type reactor equipped with two-shaft blades is a method that is effective for producing the fluoroalkylsulfonic anhydride with a high yield. For example, in the case of trifluoromethanesulfonic anhydride, its production is possible at a yield of about 85%, based on trifluoromethanesulfonic acid as the raw material. However, the unreacted trifluoromethanesulfonic acid still remains in metaphosphoric acid as the residue. Therefore, it is difficult to improve yield.

It is an object of the present invention to provide a production method to further improve yield of a fluoroalkanesulfonic anhydride.

As a result of an eager study, the present inventors have found that the unreacted fluoroalkylsulfonic acid can be recovered by reacting a fluoroalkylsulfonic acid with diphosphorus pentoxide using a kneader-type reactor equipped with two-shaft blades and then further heating the residue after discharging the fluoroalkylsulfonic anhydride as a main product from the reactor, thereby achieving the present invention.

That is, the present invention provides a method (first method) for producing a fluoroalkanesulfonic anhydride represented by the following general formula (2) by introducing a fluoroalkanesulfonic acid represented by the following formula (1) and diphosphorus pentoxide into a kneader-type reactor having a maximum power of 1.0 kW or greater per an actual capacity of 100 L and equipped with at least two-shaft blades and by kneading them in the reactor by a power of 0.5 kW or greater per an actual capacity of 100 L, the method being characterized by that the method comprises a first step of introducing the fluoroalkanesulfonic acid and diphosphorus pentoxide into the reactor such that a molar ratio of a total amount of the fluoroalkanesulfonic acid introduced to a total amount of the diphosphorus pentoxide introduced becomes 2.0 or greater, a second step in which the fluoroalkanesulfonic acid is reacted with the diphosphorus pentoxide, while kneading the fluoroalkanesulfonic acid and the diphosphorus pentoxide, which have been introduced in the first step, at a temperature in the reactor that is 40° C. or higher and is lower than 100° C., to produce the fluoroalkanesulfonic anhydride as a main product and metaphosphoric acid as a by-product, and in which the fluoroalkanesulfonic anhydride as the main product is discharged from the reactor, and a third step of discharging the unreacted fluoroalkanesulfonic acid from the reactor, while further kneading a residue in the reactor, which is obtained by the second step, at a temperature in the reactor that is 100° C. or higher and is lower than 140° C., and that the unreacted fluoroalkanesulfonic acid, which is discharged by the third step, is used as a total or part of the fluoroalkanesulfonic acid introduced in the first step.

$$R^f SO_3 H \tag{1}$$

$$(R^f SO_2)_2 O \tag{2}$$

($R^f$ in the formula represents a $C_{1-4}$ straight-chain or $C_{3-4}$ branched chain, saturated or unsaturated, fluoroalkyl group.)

The first method may be a method (second method) for producing the fluoroalkanesulfonic anhydride, which is characterized by that, in the first step, in terms of the order of introducing the fluoroalkanesulfonic acid and diphosphorus pentoxide, the fluoroalkanesulfonic acid and then diphosphorus pentoxide are introduced, or the fluoroalkanesulfonic acid and diphosphorus pentoxide are introduced simultaneously.

The second method may be a method (third method) for producing the fluoroalkanesulfonic anhydride, which is characterized by that, in the first step, when introducing diphosphorus pentoxide into the reactor, a liquid temperature of the fluoroalkanesulfonic acid is 30° C. or higher and lower than 100° C.

Any one of the first to third methods may be a method (fourth method) for producing the fluoroalkanesulfonic anhydride, which is characterized by that the fluoroalkanesulfonic anhydride, which is discharged by the second step, is liquefied and recovered by cooling.

The first method may be a method (fifth method) for producing the fluoroalkanesulfonic anhydride, which is characterized by comprising a fourth step of adding orthophosphoric acid to a residue in the reactor, which is obtained by the third step, to conduct a reaction with the metaphosphoric acid, thereby synthesizing pyrophosphoric acid, and a fifth step of discharging a residue containing the pyrophosphoric acid, which has been synthesized by the fourth step, from the reactor.

The fifth method may be a method (sixth method) for producing the fluoroalkanesulfonic anhydride, which is characterized by that water is added to a residue discharged by the fifth step to conduct a reaction with the pyrophosphoric acid in the residue, thereby synthesizing orthophosphoric acid, and that the obtained orthophosphoric acid is used as a total or part of the orthophosphoric acid added by the fourth step.

Advantageous Effect of the Invention

It is possible by the production method of the present invention to improve yield of the fluoroalkanesulfonic anhydride to 90% or higher.

DETAILED DESCRIPTION

In the following, the present invention is further described in detail.

In the production method of the present invention, there is used a kneader-type reactor having a maximum power of 1.0 kW or greater per an actual capacity of 100 L and equipped with at least two-shaft blades. Into this reactor, there are introduced a fluoroalkanesulfonic acid represented by the general formula $R^f SO_3 H$ ($R^f$ in the formula represents a $C_{1-4}$ straight-chain or $C_{3-4}$ branched chain, saturated or unsaturated, fluoroalkyl group.) and diphosphorus pentoxide. Regarding the definition of $R^f$, for convenience, a monovalent, straight-chain or branched-chain, unsaturated, fluorine-containing hydrocarbon group is referred to as an unsaturated fluoroalkyl group. In the reactor, there is produced a fluoroalkanesulfonic anhydride represented by the general formula $(R^f SO_2)_2 O$ ($R^f$ in the formula represents the same fluoroalkyl group as that of the fluoroalkanesulfonic acid as the raw material) by kneading them by a power of 0.5 kW or greater per an actual capacity of 100 L. In more detail, the production method of the present invention comprises the following steps.

(First step) The fluoroalkanesulfonic acid and diphosphorus pentoxide are introduced into the reactor such that a molar ratio of a total amount of the fluoroalkanesulfonic acid introduced to a total amount of the diphosphorus pentoxide introduced becomes 2.0 or greater.

(Second step) After the first step, while kneading the materials introduced, the fluoroalkanesulfonic acid is reacted with the diphosphorus pentoxide at a temperature in the reactor that is 40° C. or higher and is lower than 100° C., to produce the fluoroalkanesulfonic anhydride as a main product and metaphosphoric acid as a by-product, and the fluoroalkanesulfonic anhydride as the main product is discharged from the reactor.

(Third step) The unreacted fluoroalkanesulfonic acid is discharged from the reactor, while further kneading a residue in the reactor, which is obtained by the second step, at a temperature in the reactor that is 100° C. or higher and is lower than 140° C.

In the production method of the present invention, furthermore, the unreacted fluoroalkanesulfonic acid, which is discharged by the third step, is used as a total or part of the fluoroalkanesulfonic acid introduced in the first step.

In general, a kneader-type reactor has a blade for kneading a material introduced from the outside by at least one shaft in a reactor having a lid for blocking the outside air and a temperature changing means capable of heating or cooling the inside for setting the reaction temperature. Furthermore, it is equipped with an introducing port for introducing the raw material into the reactor, an exhaust portion for discharging the gas of the gas phase portion in the reactor, and a residue discharging port for discharging the residue in the reactor. As the temperature changing means, for example, there are a method of installing an electric heater in the inside or outside of the reactor, a method of installing a heat exchanger or jacket for making a coolant or heat medium flow in the inside or outside of the reactor, and the like. In general, this kneader-type reactor is a reactor used in the case of the reactant being high in viscosity, such as a chemical reaction of polymer polymerization.

Of general kneader-type reactors, a kneader-type reactor used in the present invention refers to particularly one equipped with at least two-shaft blades for kneading. The shape of the two-shaft blades is not particularly limited. For example, it is possible to use a Z-type blade, an FT-type blade, a screw-type blade, etc.

Furthermore, the rotation direction of the shaft is not particularly specified. A plurality of shafts may be rotated in the same direction or may be rotated in the opposite directions.

Furthermore, as to its power, in view of that the unreacted fluoroalkanesulfonic acid is efficiently recovered from a glassy metaphosphoric acid ($P_2O_5 \cdot H_2O$) by kneading the reaction residue in the second step, since it is preferable that the kneading is conducted in the kneader-type reactor by a power of 0.5 kW or greater per an actual capacity of 100 L, the maximum power of the reactor is preferably 1.0 kW or greater, more preferably 2.0 kW or greater, per a reactor capacity of 100 L. If the maximum power becomes smaller than 1.0 kW, it becomes difficult to conduct the kneading in a glassy metaphosphoric acid ($P_2O_5 \cdot H_2O$) by a power of 0.5 kW or greater per an actual capacity of 100 L, thereby causing a possibility that the unreacted fluoroalkanesulfonic acid cannot be efficiently recovered.

The actual capacity of a kneader-type reactor refers to the minimum amount of the liquid filled, at which a blade provided in the inside of the kneader-type reactor is at or lower than the surface of the liquid filled in the inside of the reactor even at its any rotational position. That is, it refers to the minimum filling capacity at which stirring of the filling material by the blade is substantially possible.

The fluoroalkanesulfonic acid used in the present step is one represented by the general formula $R^f SO_3H$. $R^f$ in the formula is the same as $R^f$ of the fluoroalkanesulfonic anhydride represented by the general formula $(R^f SO_2)_2O$ as the target product and represents a $C_{1-4}$ straight-chain or $C_{3-4}$ branched chain, saturated or unsaturated, fluoroalkyl group. This fluoroalkyl group is one replaced with at least one fluorine. In particular, a perfluoroalkyl group, such as trifluoromethyl group, is preferable.

Specifically, it is possible to cite trifluoromethanesulfonic acid, pentafluoroethanesulfonic acid, heptafluoropropanesulfonic acid, and nonafluorobutanesulfonic acid. Of these, more preferably, it is trifluoromethanesulfonic acid.

In the first step, the order of introducing the fluoroalkanesulfonic acid and diphosphorus pentoxide as the raw materials into the above-mentioned kneader-type reactor is not limited. They may be introduced at the same time. Alternatively, one may be introduced earlier, or they may be introduced alternately.

In the case of introducing diphosphorus pentoxide earlier, diphosphorus pentoxide tends to form aggregates in the reactor, thereby causing a possibility to increase the load on the shaft for rotating the blade. Furthermore, an aggregated material becomes inferior in reactivity, thereby causing a possibility that it is necessary for the reaction to take a long time. Therefore, it is preferable to introduce the fluoroalkanesulfonic acid and then diphosphorus pentoxide or introduce them at the same time. In this case, when introducing diphosphorus pentoxide, it is preferable that the liquid temperature of the fluoroalkanesulfonic acid in the reactor is 30° C. or higher and lower than 100° C. In the case of introducing diphosphorus pentoxide at a temperature lower than 30° C., there tend to occur aggregates of diphosphorus pentoxide in the liquid of the fluoroalkanesulfonic acid in the reactor, thereby causing a possibility to block an efficient mixing. Furthermore, it causes a possibility to increase the load on the shaft for rotating the blade.

On the other hand, if the liquid temperature of the fluoroalkanesulfonic acid in the reactor when introducing diphosphorus pentoxide is 100° C. or higher, when conducting the reaction by introducing diphosphorus pentoxide, the production of a fluoroalkanesulfonic acid ester ($R^f SO_3 R^f$) increases by the reaction shown by the following reaction formula 2. Therefore, it is not preferable.

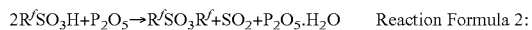   Reaction Formula 2:

Furthermore, in terms of the amounts of the fluoroalkanesulfonic acid and diphosphorus pentoxide introduced in the first step, it is preferable that the molar ratio of the fluoroalkanesulfonic acid to diphosphorus pentoxide is at least two. If the molar ratio is less than 2, viscosity of metaphosphoric acid ($P_2O_5 \cdot H_2O$) as the reaction residue after the reaction becomes too high, thereby causing a possibility that the kneading becomes difficult, even if applying a power of 0.5 kW or greater using the above-mentioned kneader-type reactor. As the amount of the fluoroalkanesulfonic acid increases, viscosity upon kneading becomes lower, thereby causing no problem in terms of driving the blade. Therefore, the upper limit of the molar ratio is not particularly limited. In view of the efficiency, however, when the molar ratio becomes 3.0 or greater, the amount of the unreacted fluoroalkanesulfonic acid increases. With this, the capacity of the reactor necessary for the amount of the main product becomes larger. Furthermore, there also increases the energy necessary for heating or the like when discharging the unreacted fluoroalkanesulfonic acid. Therefore, it is preferably less than 3.0, more preferably less than 2.5.

The temperature range in the inside of the kneader-type reactor in the second step is preferably 40° C. or higher and lower than 100° C. At a value lower than 40° C., viscosity of the reaction residue becomes too high, thereby causing a possibility that the kneading becomes difficult, even if applying a power of 0.5 kW or greater using the kneader-type reactor. On the other hand, at a temperature of 100° C. or higher, a decomposition reaction shown by the following reaction formula 3 tends to occur. This produces a fluoroalkanesulfonic acid ester ($R^f SO_3 R^f$) as a by-product, thereby causing a possibility to lower yield of the fluoroalkanesulfonic anhydride as the target product.

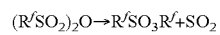   Reaction Formula 3:

In the second step, as to the method for discharging the fluoroalkanesulfonic anhydride, it is possible to use a method in which in general an inert gas, such as helium, argon, nitrogen or carbon dioxide, is introduced into the reactor, thereby evaporating the fluoroalkanesulfonic anhydride into the inert gas and then purging to discharge the same to be accompanied by the inert gas, or a method in which the reactor is decompressed by using a suction means such as vacuum pump, thereby discharging the fluoroalkanesulfonic anhydride which is evaporated. Considering productivity, it is preferable to use a method of exhausting the reactor by using an exhausting means such as vacuum pump.

The pressure range of the inside of the reactor upon suction using a suction means is not particularly specified. It is, however, preferable to be a pressure range in which the operation is easy, since the discharge is conducted by evaporation of the fluoroalkanesulfonic anhydride as a main product of the reaction. Specifically, it is preferable to conduct the suction until a pressure of a range from 0.1 kPa to less than 50 kPa. For a pressure lower than 0.1 kPa, in view of a practical operation, it is necessary to use one that is particularly large in terms of performance of the suction means, such as vacuum pump. Furthermore, at a pressure of 50 kPa or higher, there lowers the amount of evaporation of the fluoroalkanesulfonic anhydride in the reactor, thereby causing a possibility that a desired productivity cannot be obtained.

The fluoroalkanesulfonic anhydride discharged from the reactor in the second step may be recovered as it is, or can be recovered through liquefaction by cooling. The cooling temperature for the liquefaction recovery is not particularly specified, as long as it is a temperature at which the fluoroalkanesulfonic anhydride condenses and liquefies. In order to improve recovery of the fluoroalkanesulfonic anhydride, it is preferable to conduct the cooling until 10° C. or lower. As an apparatus for the recovery, it is possible to cite, for example, a shell and tube type heat exchanger. The form of the apparatus is not limited as long as it is a means capable of conducting the liquefaction recovery by cooling.

After the second step, it proceeds to the third step by further increasing the temperature of the kneader-type reactor.

In the third step, the temperature range in the inside of the reactor is preferably 100° C. or higher and lower than 140° C. At a temperature lower than 100° C., it becomes difficult to evaporate the unreacted fluoroalkanesulfonic acid from the residue obtained by the second step, thereby making its discharge difficult. At a temperature of 140° C. or higher, a reaction similar to the reaction formula 2 tends to occur. Therefore, there is a risk that the fluoroalkanesulfonic acid ester as a by-product is produced, and thereby recovery of the unreacted fluoroalkanesulfonic acid lowers.

As to the method for discharging the unreacted fluoroalkanesulfonic acid in the third step, it is considered a method in which in general an inert gas, such as helium, argon, nitrogen or carbon dioxide, is introduced into the reactor, thereby evaporating the fluoroalkanesulfonic acid into the inert gas and then purging to discharge the same to be accompanied by the inert gas, or a method in which the reactor is decompressed by using a suction means such as vacuum pump, thereby discharging the fluoroalkanesulfonic acid which is evaporated. Considering productivity, it is preferable to use a method of exhausting the reactor by using an exhausting means such as vacuum pump.

The pressure range of the inside of the reactor upon suction using a suction means is not particularly specified. It is, however, preferable to be a pressure range in which the distillation is easy, since the unreacted fluoroalkanesulfonic acid is distilled out. Specifically, it is preferable to conduct the suction until a pressure of a range from 0.1 kPa to less than 25 kPa. For a pressure lower than 0.1 kPa, in view of a practical operation, it is necessary to use one that is particularly large in terms of performance of the suction means, such as vacuum pump. Furthermore, at a pressure of 25 kPa or higher, there lowers the amount of evaporation of the unreacted fluoroalkanesulfonic acid in the reactor, thereby causing a possibility that a desired productivity cannot be obtained. In comparison between the second step and the third step, the discharge rate tends to be lower in the third step than in the second step. In order to make the discharge rates of the second and third steps at around the same level, it is preferable that the pressure in the reactor is lower in the third step than in the second step.

In the third step, the unreacted fluoroalkanesulfonic acid, which is discharged from the reactor, may be recovered as it is, or can be recovered through liquefaction by cooling. The cooling temperature for the liquefaction recovery is not particularly specified, as long as it is a temperature at which the fluoroalkanesulfonic acid condenses and liquefies. In order to improve recovery of the fluoroalkanesulfonic acid, it is more preferable to conduct the cooling until 10° C. or lower. As an apparatus for the recovery, it is possible to cite, for example, a shell and tube type heat exchanger. The form of the apparatus is not limited as long as it is a means capable of conducting the liquefaction recovery by cooling.

The unreacted fluoroalkanesulfonic acid in the evaporated matter discharged in the third step has a high purity, roughly 90 wt % or higher. Besides, the fluoroalkanesulfonic anhydride or fluoroalkanesulfonic acid ester is contained. Therefore, the unreacted fluoroalkanesulfonic acid, which is discharged, can be used as it is for superacid use, etc. Furthermore, it can be used again as the raw material portion for synthesizing the fluoroalkanesulfonic anhydride. By using it again as a part or total of the fluoroalkanesulfonic acid as the raw material introduced in the first step, it is possible to improve yield of the fluoroalkanesulfonic anhydride. In this case, the unreacted fluoroalkanesulfonic acid, which is discharged, may be used by a direct introduction or may be used by introducing one recovered through liquefaction. Furthermore, the unreacted fluoroalkanesulfonic acid recovered by conducting the third step several times may be stored in a tank and may be used as the raw material of the first step when stored by a predetermined amount.

In the kneader-type reactor after the end of the third step, metaphosphoric acid ($P_2O_5.H_2O$) remains as the residue. Metaphosphoric acid is a glassy, high-viscosity material in a temperature range of 100-140° C. Thus, it is difficult to take that out of the reactor by a normal method, such as the liquid transfer by piping. Therefore, it is possible to take the residue out by dissolving in water or the like in order to take that out after reducing viscosity by a certain degree.

In case that metaphosphoric acid has directly been dissolved in water, the phosphoric acid concentration of the water increases in the course of dissolution of the metaphosphoric acid. At a stage when the metaphosphoric acid has finally and completely been dissolved, it becomes a phosphoric acid aqueous solution having a composition of $P_2O_5.nH_2O$ ($3.0 \le n < 7.9$).

The phosphoric acid aqueous solution may, however, strikingly corrode a metal material constituting the kneader-type reactor. Therefore, since water is not used to dissolve the residue by adding orthophosphoric acid to the residue formed in the kneader-type reactor in the third step to conduct a reaction with metaphosphoric acid in the residue to synthesize pyrophosphoric acid (the fourth step) and taking the residue containing the synthesized pyrophosphoric acid out of the reactor (the fifth step), and since metaphosphoric acid, orthophosphoric acid and pyrophosphoric acid, which are introduced into or formed in the reactor, do not corrode metal materials, it is possible to use not only a low-strength, corrosion-resistance material, such as glass lining and polytetrafluoroethylene lining, but also a high-strength metal material, such as stainless steel, for the blade of the kneader-type reactor and a portion of the reactor, piping, etc., with which the residue is brought into contact. Furthermore, pyrophosphoric acid, which is synthesized in the fourth step, is lower in viscosity as compared with metaphosphoric acid and is in a liquid form in a temperature range of from 60° C. to 600° C. so as to be easy to transfer the liquid by piping. Therefore, it is possible to easily take out the residue in the reactor. At a temperature higher than 600° C., pyrophosphoric acid turns to gas and cannot keep a liquid form. Therefore, it is not preferable.

Next, a method for reusing the pyrophosphoric-acid-containing residue taken out is explained. The residue taken out solidifies at 60° C. or lower. Normally, it is preferable to take that into a container that can be maintained at a temperature of 70° C. to 600° C.

Furthermore, it is possible to synthesize orthophosphoric acid by adding water to the residue taken out, to conduct a reaction with pyrophosphoric acid in the residue. As to the amount of water to be added, a method of the addition is taken, based on the amount of diphosphorus pentoxide to be added in the first step. Specifically, it is added by the rate of 0.12 kg or greater and less than 0.76 kg per 1 kg of diphosphorus pentoxide added in the first step. If it is less than 0.12 kg, it is not possible to sufficiently lower viscosity of pyrophosphoric acid to be added. Therefore, it is not preferable. Furthermore, in the case of being 0.76 kg or greater, it has a concentration at which the metal material is corroded. Therefore, similarly, it is not preferable.

A reaction vessel that is used for conducting a reaction with pyrophosphoric acid in the residue by adding water is preferably one of a corrosion-resistance material due to the addition of water. Furthermore, it is desirably a heating-type one that can be maintained at a temperature of from 70° C. to 600° C.

As the material of the reaction vessel, it is possible to cite, for example, glass lining, polytetrafluoroethylene lining or PFA lining, etc. From these corrosion-resistance materials, it is preferable to select one that is heat resistant against the desired temperature. For example, in the case of glass lining, the desired temperature can be selected until 600° C. In the case of polytetrafluoroethylene lining or PFA lining, the desired temperature can be selected until 260° C.

Furthermore, as to the addition of water, the liquid transfer is possible by using a normal liquid transfer means, such as magnet pump, diaphragm pump, syringe pump, plunger pump, bellows pump, gear pump, syringe pump, tubing pump, etc. It is also possible to use a liquid transfer means using a head difference. Furthermore, one that is suitably capable of adjusting the amounts of the residue taken out and the water to be added, according to the required amount of orthophosphoric acid, is preferable. Thus, it is preferable to use, for example, magnet pump, diaphragm pump, etc.

The orthophosphoric acid synthesized from the residue containing pyrophosphoric acid taken out can be used as a part or total of the orthophosphoric acid used to be reacted with metaphosphoric acid in the fourth step. Therefore, it is possible to reduce usage of phosphoric acid used for the dissolution.

As to the fluoroalkanesulfonic anhydride obtained by the present invention, it is possible to obtain one already sufficiently high in purity. For a further purification, the obtained fluoroalkanesulfonic anhydride may be subjected to rectification.

As the rectification method, for example, using a rectification tower, the obtained fluoroalkanesulfonic anhydride is put into a reboiler of the rectification tower, followed by boiling at a temperature of 30° C. or greater and lower than 100° C. to conduct the rectification. By doing so, it is possible to obtain a further purified fluoroalkanesulfonic anhydride. In the case of conducting the boiling at a temperature of 100° C. or higher, there tends to occur as shown in the above reaction formula 3 a decomposition reaction of the fluoroalkanesulfonic anhydride. There is a possibility that this decomposition reaction generates a fluoroalkanesulfonic acid ester to lower yield of the fluoroalkanesulfonic anhydride.

In the case of conducting the rectification in a rectification tower, the fluoroalkanesulfonic acid and the fluoroalkanesulfonic anhydride are contained in the rectification residue remaining in the reboiler after the rectification. This rectification residue can be used again as the fluoroalkanesulfonic acid, which is the raw material of the first step.

In the following, one embodiment of the present invention is explained in detail by examples, but the present invention is not limited to such examples.

Example 1

A kneader-type reactor (actual capacity: 400 L; maximum power: 45 kW) equipped with a jacket and two-shaft blades was charged with 430.0 kg of trifluoromethanesulfonic acid of 99.5 wt % purity, followed by making warm water flow through the jacket to increase temperature of the introduced trifluoromethanesulfonic acid to 40° C. Then, under a condition that the inside of the reactor was stirred, 180.0 kg of diphosphorus pentoxide powder of 98.5 wt % purity (molar ratio of trifluoromethanesulfonic acid to diphosphorus pentoxide was 2.3) was added. Then, temperature of the warm water flowing through the jacket was increased. To correspond to the second step, while the inside of the reactor was kneaded by a power of 8 kW, the inside temperature of the reactor was increased to 90° C. to generate trifluoromethanesulfonic anhydride, and the inside of the reactor was sucked by using a vacuum pump connected to the reactor to conduct an operation of discharging the generated trifluoromethanesulfonic anhydride from the reactor. The trifluoromethanesulfonic anhydride discharged from the kneader-type reactor was subjected to a liquefaction condensation by cooling at 10° C. using a shell and tube type cooler installed in the middle of piping connecting the reactor with the vacuum pump. The liquefied trifluoromethanesulfonic anhydride was recovered in a product tank. The recovered trifluoromethanesulfonic anhydride was 317.8 kg in weight. As purity of the recovered product was analyzed by using an NMR measurement apparatus (JNM-AL400, made by JEOL), purity was 97.7 wt %.

Then, the warm medium made to flow through the jacket of the kneader-type reactor was changed from warm water to steam, and there was conducted an operation for discharging the unreacted trifluoromethanesulfonic acid from the reactor, which corresponded to the third step, by increasing the inside temperature of the kneader-type reactor until 120° C. and by sucking the inside of the reactor using a vacuum pump connected to the reactor, while kneading the residue of the reactor at a power of 10 kW. The unreacted trifluoromethanesulfonic acid discharged from the reactor was subjected to a liquefaction condensation by cooling to 10° C. using a shell and tube type cooler installed in the middle of the piping connecting the reactor with the vacuum pump. The liquefied trifluoromethanesulfonic acid was recovered in a tank for recovering the unreacted trifluoromethanesulfonic acid. The recovered trifluoromethanesulfonic acid was 85.0 kg in weight. As composition of the recovered product was analyzed by using an NMR measurement apparatus (JNM-AL400, made by JEOL), purity of trifluoromethanesulfonic acid was 98.9 wt %, trifluoromethanesulfonic anhydride was 0.5 wt %, and the trifluoromethanesulfonic acid ester was 0.6 wt %.

Yield of trifluoromethanesulfonic anhydride was found to be 96.1% by conducting a calculation based on trifluoromethanesulfonic acid from which the recovered, unreacted trifluoromethanesulfonic acid was subtracted. 85.0 kg of the recovered, unreacted trifluoromethanesulfonic acid was totally used as the raw material of the next batch.

Example 2

Using an apparatus similar to that of Example 1, the test was conducted. After charging a kneader-type reactor with 315.5 kg of trifluoromethanesulfonic acid having a purity of 99.5 wt %, it was charged with 85.0 kg of the unreacted, recovered trifluoromethanesulfonic acid of 98.9 wt % purity recovered in Example 1. Then, the introduced trifluoromethanesulfonic acid was maintained at 40° C., followed by adding 180.0 kg (the molar ratio of trifluoromethanesulfonic acid to diphosphorus pentoxide was 2.1) of a diphosphorus pentoxide powder of 98.5 wt % purity in a condition that the inside of the reactor was stirred. As to the other conditions, it was conducted under the same conditions as those of Example 1.

The recovered trifluoromethanesulfonic anhydride was 312.8 kg in weight. As purity of trifluoromethanesulfonic anhydride in the recovered product was analyzed by using an NMR measurement apparatus (JNM-AL400, mad by JEOL), it was 98.0 wt %.

Furthermore, the recovered, unreacted trifluoromethanesulfonic acid was 58.6 kg in weight. In composition of the recovered product, purity of trifluoromethanesulfonic acid was 98.2 wt %, trifluoromethanesulfonic anhydride was 1.1 wt %, and trifluoromethanesulfonic acid ester was 0.7 wt %.

Yield of trifluoromethanesulfonic anhydride was found to be 95.8% by conducting a calculation based on trifluoromethanesulfonic acid from which the recovered, unreacted trifluoromethanesulfonic acid was subtracted. 58.6 kg of the recovered, unreacted trifluoromethanesulfonic acid was totally used as the raw material of another batch.

Example 3

Using an apparatus similar to that of Example 1, the test was conducted. The kneader-type reactor was charged with 451.2 kg of trifluoromethanesulfonic acid of 99.5 wt % purity, followed by making warm water flow through the jacket to maintain the introduced trifluoromethanesulfonic acid at 40° C. Under a condition that the inside of the reactor was stirred, 150.0 kg of diphosphorus pentoxide powder of 98.5 wt % purity (molar ratio of trifluoromethanesulfonic acid to diphosphorus pentoxide was 2.9) was added. Then, temperature of the warm water flowing through the jacket was increased. To correspond to the second step, while the inside of the reactor was kneaded by a power of 8 kW, the inside temperature of the reactor was increased to 90° C. to generate trifluoromethanesulfonic anhydride, and the inside of the reactor was sucked by using a vacuum pump connected to the reactor to conduct an operation of discharging the generated trifluoromethanesulfonic anhydride from the reactor. The trifluoromethanesulfonic anhydride discharged from the reactor was subjected to a liquefaction condensation by cooling at 10° C. using a shell and tube type cooler installed in the middle of piping connecting the reactor with the vacuum pump. The liquefied trifluoromethanesulfonic anhydride was recovered in a product tank. The recovered trifluoromethanesulfonic anhydride was 251.2 kg in weight. Purity was 97.1 wt %.

Then, the warm medium made to flow through the jacket of the kneader-type reactor was changed from warm water to steam, and there was conducted an operation for discharging the unreacted trifluoromethanesulfonic acid from the reactor, which corresponded to the third step, by increasing the inside temperature of the reactor until 120° C. and by sucking the inside of the reactor using a vacuum pump connected to the reactor, while kneading the residue of the reactor at a power of 10 kW. The unreacted trifluoromethanesulfonic acid discharged from the reactor was subjected to a liquefaction condensation by cooling to 10° C. using a shell and tube type cooler installed in the middle of the piping connecting the reactor with the vacuum pump. The liquefied trifluoromethanesulfonic acid was recovered in a tank for recovering the unreacted trifluoromethanesulfonic acid. The recovered trifluoromethanesulfonic acid was 171.2 kg in weight. As to composition of the recovered product, trifluoromethanesulfonic acid was 98.1 wt %, trifluoromethanesulfonic anhydride was 1.3 wt %, and the trifluoromethanesulfonic acid ester was 0.6 wt %.

Yield of trifluoromethanesulfonic anhydride was found to be 92.4% by conducting a calculation based on trifluoromethanesulfonic acid from which the recovered, unreacted trifluoromethanesulfonic acid was subtracted. 171.2 kg of the recovered, unreacted trifluoromethanesulfonic acid was totally used as the raw material of another batch.

Example 4

Using an apparatus similar to that of Example 1, the test was conducted. The kneader-type reactor was charged with 430.0 kg of trifluoromethanesulfonic acid of 99.5 wt % purity, followed by making warm water flow through the jacket to maintain the introduced trifluoromethanesulfonic acid at 40° C. Under a condition that the inside of the reactor was stirred, 180.0 kg of diphosphorus pentoxide powder of 98.5 wt % purity (molar ratio of trifluoromethanesulfonic acid to diphosphorus pentoxide was 2.3) was added. Then, temperature of the warm water flowing through the jacket was adjusted. To correspond to the second step, while the inside of the reactor was kneaded by a power of 8 kW, the inside temperature of the reactor was increased to 45° C. to generate trifluoromethanesulfonic anhydride, and the inside of the reactor was sucked by using a vacuum pump connected to the reactor to conduct an operation of discharging the generated trifluoromethanesulfonic anhydride from the reactor. The trifluoromethanesulfonic anhydride discharged from the kneader-type reactor was subjected to a liquefaction condensation by cooling at 10° C. using a shell and tube type cooler installed in the middle of piping connecting the reactor with the vacuum pump. The liquefied trifluoromethanesulfonic anhydride was recovered in a product tank. The recovered trifluoromethanesulfonic anhydride was 289.5 kg in weight. As purity of the recovered product was analyzed by using an NMR measurement apparatus (JNM-AL400, made by JEOL), purity was 98.8 wt %.

Then, the heat medium made to flow through the jacket of the kneader-type reactor was changed from warm water to steam, and there was conducted an operation for discharging the unreacted trifluoromethanesulfonic acid from the reactor, which corresponded to the third step, by increasing the inside temperature of the reactor until 120° C. and by sucking the inside of the reactor using a vacuum pump connected to the reactor, while kneading the residue of the reactor at a power of 10 kW. The unreacted trifluoromethanesulfonic acid discharged from the reactor was subjected to a liquefaction condensation by cooling to 10° C. using a shell and tube type cooler installed in the middle of the piping connecting the reactor with the vacuum pump. The liquefied trifluoromethanesulfonic acid was recovered in a tank for recovering the unreacted trifluoromethanesulfonic acid. The recovered trifluoromethanesulfonic acid was 114.5 kg in weight. As composition of the recovered product was analyzed by using an NMR measurement apparatus (JNM-AL400, made by JEOL), purity of trifluoromethanesulfonic acid was 93.5 wt %, trifluoromethanesulfonic anhydride was 5.9 wt %, and the trifluoromethanesulfonic acid ester was 0.6 wt %.

Yield of trifluoromethanesulfonic anhydride was found to be 94.9% by conducting a calculation based on trifluoromethanesulfonic acid from which the recovered, unreacted trifluoromethanesulfonic acid was subtracted. 114.5 kg of the recovered, unreacted trifluoromethanesulfonic acid was used as the raw material of another batch.

Example 5

Using an apparatus similar to that of Example 1, the test was conducted. The kneader-type reactor was charged with 374.8 kg of trifluoromethanesulfonic acid of 99.5 wt % purity, followed by charging with 58.6 kg of the unreacted, recovered trifluoromethanesulfonic acid of 93.5 wt % purity recovered in Example 4. Then, the introduced trifluoromethanesulfonic acid was maintained at 40° C. Under a condition that the inside of the reactor was stirred, 180.0 kg of diphosphorus pentoxide powder of 98.5 wt % purity (molar ratio of trifluoromethanesulfonic acid to diphosphorus pentoxide was 2.3) was added. Then, temperature of the warm water flowing through the jacket was increased. To correspond to the second step, while the inside of the reactor was kneaded by a power of 8 kW, the inside temperature of the reactor was increased to 90° C. to generate trifluoromethanesulfonic anhydride, and the inside of the reactor was sucked by using a vacuum pump connected to the reactor to conduct an operation of discharging the generated trifluoromethanesulfonic anhydride from the reactor. The trifluoromethanesulfonic anhydride discharged from the reactor was subjected to a liquefaction condensation by cooling at 10° C. using a shell and tube type cooler installed in the middle of piping connecting the reactor with the vacuum pump. The liquefied trifluoromethanesulfonic anhydride was recovered in a product tank. The recovered trifluoromethanesulfonic anhydride was 315.4 kg in weight. Purity was 97.6 wt %.

Then, the warm medium made to flow through the jacket of the kneader-type reactor was changed from warm water to steam, and there was conducted an operation for discharging the unreacted trifluoromethanesulfonic acid from the reactor, which corresponded to the third step, by increasing the inside temperature of the reactor until 138° C. and by sucking the inside of the reactor using a vacuum pump connected to the reactor, while kneading the residue of the reactor at a power of 10 kW. The unreacted trifluoromethanesulfonic acid discharged from the reactor was subjected to a liquefaction condensation by cooling to 10° C. using a shell and tube type cooler installed in the middle of the piping connecting the reactor with the vacuum pump. The liquefied trifluoromethanesulfonic acid was recovered in a tank for recovering the unreacted trifluoromethanesulfonic acid. The recovered trifluoromethanesulfonic acid was 92.1 kg in weight. As composition of the recovered product was analyzed, purity of trifluoromethanesulfonic acid was 92.4 wt %, trifluoromethanesulfonic anhydride was 0.6 wt %, and the trifluoromethanesulfonic acid ester was 7.0 wt %.

Yield of trifluoromethanesulfonic anhydride was found to be 95.6% by conducting a calculation based on trifluoromethanesulfonic acid from which the recovered, unreacted trifluoromethanesulfonic acid was subtracted. 92.1 kg of the recovered, unreacted trifluoromethanesulfonic acid was totally used as the raw material of another batch.

Example 6

In a kneader-type reactor (actual capacity: 400 L; maximum power: 45 kW) equipped with a jacket and two-shaft blades, warm water was allowed to flow through the jacket to increase temperature of the inside of the reactor to 40° C. Then, under a condition that the blades in the inside of the reactor were rotated, 430.0 kg of trifluoromethanesulfonic acid of 99.5 wt % purity and 180.0 kg of diphosphorus pentoxide powder of 98.5 wt % purity (molar ratio of trifluoromethanesulfonic acid to diphosphorus pentoxide was 2.3) were simultaneously introduced into the reactor. Then, temperature of the warm water flowing through the jacket was increased. To correspond to the second step, while the inside of the reactor was kneaded by a power of 8 kW, the inside temperature of the reactor was increased to 90° C. to generate trifluoromethanesulfonic anhydride, and the inside of the reactor was sucked by using a vacuum pump connected to the reactor to conduct an operation of discharging the generated trifluoromethanesulfonic anhydride from the reactor. The trifluoromethanesulfonic anhydride discharged from the reactor was subjected to a liquefaction condensation by cooling at 10° C. using a shell and tube type cooler installed in the middle of piping connecting the reactor with the vacuum pump. During the reaction, aggregates partly occurred in the inside of the kneader-type reactor. As a result, it was necessary to take a long period of time until all of the aggregates underwent the reaction. In the end, it was necessary to take a reaction time twice that of Example 1. The recovered trifluoromethanesulfonic anhydride was 319.8 kg in weight. As purity of the recovered product was analyzed by using an NMR measurement apparatus (JNM-AL400, made by JEOL), purity was 97.2 wt %.

Then, the heat medium made to flow through the jacket of the kneader-type reactor was changed from warm water to steam, and there was conducted an operation for discharging the unreacted trifluoromethanesulfonic acid from the reactor, which corresponded to the third step, by increasing the inside temperature of the reactor until 120° C. and by sucking the inside of the reactor using a vacuum pump connected to the reactor, while kneading the residue of the reactor at a power of 10 kW. The unreacted trifluoromethanesulfonic acid discharged from the reactor was subjected to a liquefaction condensation by cooling to 10° C. using a shell and tube type cooler installed in the middle of the piping connecting the reactor with the vacuum pump. The liquefied trifluoromethanesulfonic acid was recovered in a tank for recovering the unreacted trifluoromethanesulfonic acid. The recovered trifluoromethanesulfonic acid was 84.8 kg in weight. As composition of the recovered product was analyzed, purity of trifluoromethanesulfonic acid was 97.4 wt %, trifluoromethanesulfonic anhydride was 1.1 wt %, and the trifluoromethanesulfonic acid ester was 1.5 wt %.

As yield of trifluoromethanesulfonic anhydride was calculated based on trifluoromethanesulfonic acid from which the recovered, unreacted trifluoromethanesulfonic acid was subtracted, it was found to be 95.8%. 84.8 kg of the recovered, unreacted trifluoromethanesulfonic acid was totally used as the raw material of the next batch.

Example 7

The test was conducted by using an apparatus similar to that of Example 1. In the kneader-type reactor, warm water was allowed to flow through the jacket to increase temperature of the inside of the reactor to 40° C. Then, under a condition that the blades in the inside of the reactor were rotated, 180.0 kg of diphosphorus pentoxide powder of 98.5 wt % purity was introduced. Then, 353.3 kg of trifluoromethanesulfonic acid of 99.5 wt % purity was introduced, followed by introducing 84.8 kg of the unreacted trifluoromethanesulfonic acid recovered in Example 6 (the molar ratio of trifluoromethanesulfonic acid to diphosphorus pentoxide was 2.3). Then, temperature of the warm water of the jacket was changed. To correspond to the second step, while the inside of the reactor was kneaded by a power of 8 kW, the inside temperature of the reactor was increased to 90° C. to generate trifluoromethanesulfonic anhydride, and the inside of the reactor was sucked by using a vacuum pump connected to the reactor to conduct an operation of discharging the generated trifluoromethanesulfonic anhydride from the reactor. The trifluoromethanesulfonic anhydride discharged from the reactor was subjected to a liquefaction condensation by cooling at 10° C. using a shell and tube type cooler installed in the middle of piping connecting the reactor with the vacuum pump. During the reaction, aggregates partly occurred in the inside of the kneader-type reactor. As a result, it was necessary to take a long period of time until all of the aggregates underwent the reaction. In the end, it was necessary to take a reaction time 2.5 times that of Example 1. The recovered trifluoromethanesulfonic anhydride was 314.5 kg in weight. Purity of trifluoromethanesulfonic anhydride was 98.0 wt %.

Then, the heat medium made to flow through the jacket of the kneader-type reactor was changed from warm water to steam, and there was conducted an operation for discharging the unreacted trifluoromethanesulfonic acid from the reactor, which corresponded to the third step, by increasing the inside temperature of the reactor until 120° C. and by sucking the inside of the reactor using a vacuum pump connected to the reactor, while kneading the residue of the reactor at a power of 10 kW. The unreacted trifluoromethanesulfonic acid discharged from the reactor was subjected to a liquefaction condensation by cooling to 10° C. using a shell and tube type cooler installed in the middle of the piping connecting the reactor with the vacuum pump. The liquefied trifluoromethanesulfonic acid was recovered in a tank for recovering the unreacted trifluoromethanesulfonic acid. The recovered trifluoromethanesulfonic acid was 82.6 kg in weight. As to composition of the recovered product, purity of trifluoromethanesulfonic acid was 98.2 wt %, trifluoromethanesulfonic anhydride was 1.1 wt %, and the trifluoromethanesulfonic acid ester was 0.7 wt %.

As yield of trifluoromethanesulfonic anhydride was calculated based on trifluoromethanesulfonic acid from which the recovered, unreacted trifluoromethanesulfonic acid was subtracted, it was found to be 92.9%. 82.6 kg of the recovered, unreacted trifluoromethanesulfonic acid was totally used as the raw material of another batch.

Example 8

Using an apparatus similar to that of Example 1, the test was conducted. The kneader-type reactor was charged with 430.0 kg of trifluoromethanesulfonic acid of 99.5 wt % purity, followed by making warm water flow through the jacket to maintain the introduced trifluoromethanesulfonic acid at 80° C. Under a condition that the inside of the reactor was stirred, 180.0 kg of diphosphorus pentoxide powder of 98.5 wt % purity (molar ratio of trifluoromethanesulfonic acid to diphosphorus pentoxide was 2.3) was added. Then, temperature of the warm water flowing through the jacket was changed. To correspond to the second step, while the inside of the reactor was kneaded by a power of 8 kW, the inside temperature of the reactor was increased to 90° C. to generate trifluoromethanesulfonic anhydride, and the inside of the reactor was sucked by using a vacuum pump connected to the reactor to conduct an operation of discharging the generated trifluoromethanesulfonic anhydride from the reactor. The trifluoromethanesulfonic anhydride discharged from the reactor was subjected to a liquefaction condensation by cooling at 10° C. using a shell and tube type cooler installed in the middle of piping connecting the reactor with the vacuum pump. The liquefied trifluoromethanesulfonic anhydride was recovered in a product tank. The recovered trifluoromethanesulfonic anhydride was 327.5 kg in weight. Purity of the trifluoromethanesulfonic anhydride was 94.0 wt %.

Then, the heat medium made to flow through the jacket of the kneader-type reactor was changed from warm water to steam, and there was conducted an operation for discharging the unreacted trifluoromethanesulfonic acid from the reactor, which corresponded to the third step, by increasing the inside temperature of the reactor until 120° C. and by sucking the inside of the reactor using a vacuum pump connected to the reactor, while kneading the residue of the reactor at a power of 10 kW. The unreacted trifluoromethanesulfonic acid discharged from the reactor was subjected to a liquefaction condensation by cooling to 10° C. using a shell and tube type cooler installed in the middle of the piping connecting the reactor with the vacuum pump. The liquefied trifluoromethanesulfonic acid was recovered in a tank for recovering the unreacted trifluoromethanesulfonic acid. The recovered trifluoromethanesulfonic acid was 87.2 kg in weight. Purity of the trifluoromethanesulfonic acid was 97.7 wt %, trifluoromethanesulfonic anhydride was 1.1 wt %, and the trifluoromethanesulfonic acid ester was 1.2 wt %.

Yield of trifluoromethanesulfonic anhydride was found to be 95.6% by conducting a calculation based on trifluoromethanesulfonic acid from which the recovered, unreacted trifluoromethanesulfonic acid was subtracted. 87.2 kg of the recovered, unreacted trifluoromethanesulfonic acid was totally used as the raw material of another batch.

Example 9

Using an apparatus similar to that of Example 1, the test was conducted. The kneader-type reactor was charged with 430.0 kg of trifluoromethanesulfonic acid of 99.5 wt % purity. Under a condition that the inside of the reactor was at room temperature (25° C.), 180.0 kg of diphosphorus pentoxide powder of 98.5 wt % purity (molar ratio of trifluoromethanesulfonic acid to diphosphorus pentoxide was 2.3) was added. Then, warm water was allowed to flow through the jacket. To correspond to the second step, while the inside of the reactor was kneaded by a power of 8 kW, the inside temperature of the reactor was increased to 90° C. to generate trifluoromethanesulfonic anhydride, and the inside of the reactor was sucked by using a vacuum pump connected to the reactor to conduct an operation of discharging the generated trifluoromethanesulfonic anhydride from the reactor. The trifluoromethanesulfonic anhydride discharged from the reactor was subjected to a liquefaction condensation by cooling at 10° C. using a shell and tube type cooler installed in the middle of piping connecting the reactor with the vacuum pump. During the reaction, many aggregates occurred in the inside of the kneader-type reactor. As a result, it was necessary to take a long period of time until all of the aggregates underwent the reaction. In the end, it was necessary to take a reaction time 2.5 times that of Example 1. The recovered trifluoromethanesulfonic anhydride was 316.2 kg in weight. Purity of the recovered product was analyzed by using an NMR measurement apparatus (JNM-AL400, made by JEOL). As a result, purity was 95.5 wt %.

Then, the heat medium made to flow through the jacket of the kneader-type reactor was changed from warm water to steam, and there was conducted an operation for discharging the unreacted trifluoromethanesulfonic acid from the reactor, which corresponded to the third step, by increasing the inside temperature of the reactor until 120° C. and by sucking the inside of the reactor using a vacuum pump connected to the reactor, while kneading the residue of the reactor at a power of 10 kW. The unreacted trifluoromethanesulfonic acid discharged from the reactor was subjected to a liquefaction condensation by cooling to 10° C. using a shell and tube type cooler installed in the middle of the piping connecting the reactor with the vacuum pump. The liquefied trifluoromethanesulfonic acid was recovered in a tank for recovering the unreacted trifluoromethanesulfonic acid. The recovered trifluoromethanesulfonic acid was 84.2 kg in weight. Composition of the recovered product was analyzed by using an NMR measurement apparatus (JNM-AL400, made by JEOL). As a result, purity of trifluoromethanesulfonic acid was 97.4 wt %, trifluoromethanesulfonic anhydride was 2.1 wt %, and the trifluoromethanesulfonic acid ester was 0.5 wt %.

As yield of trifluoromethanesulfonic anhydride was calculated based on trifluoromethanesulfonic acid from which the recovered, unreacted trifluoromethanesulfonic acid was subtracted, it was found to be 92.9%. 84.2 kg of the recovered, unreacted trifluoromethanesulfonic acid was totally used as the raw material of another batch.

Example 10

To correspond to the third step in Example 1, while kneading the residue in the kneader-type reactor at a power of 10 kW, the unreacted trifluoromethanesulfonic acid was discharged from the reactor by sucking the inside of the reactor using a vacuum pump connected to the reactor. To 216.0 Kg of the subsequent residue (94.0 wt % was metaphosphoric acid), 127.0 Kg of orthophosphoric acid was added to conduct a reaction with the residue, thereby synthesizing pyrophosphoric acid in the inside of the reactor. This pyrophosphoric acid (liquid) was transferred to an outside, receiving tank by pressure difference.

Next, to 343.0 Kg of the residue (95.0 wt % was pyrophosphoric acid) in this outside, receiving tank, 88.0 Kg of water (0.49 kg relative to 1 kg of diphosphorus pentoxide) was added to conduct a reaction with pyrophosphoric acid, thereby synthesizing orthophosphoric acid of 96.0 wt % purity. Herein, using 127.0 Kg of the synthesized orthophosphoric acid, to correspond to the third step in Example 2, while kneading the residue in the kneader-type reactor at a power of 10 kW, the unreacted trifluoromethanesulfonic acid was discharged from the reactor by sucking the inside of the reactor using a vacuum pump connected to the reactor, followed by an addition to the residue in the inside of the kneader-type reactor and then, similar to the above, a transfer of the residue (liquid) in the inside of the reactor to the outside, receiving tank.

Example 11

After repeating Example 10 thirty times, it was found in the inside of the kneader-type reactor that metallic luster was still maintained and that there was no occurrence of corrosion by phosphoric acid water.

Comparative Example 1

Using an apparatus similar to that of Example 1, the test was conducted. The kneader-type reactor was charged with 352.6 kg of trifluoromethanesulfonic acid of 99.5 wt % purity, followed by making warm water flow through the jacket to maintain the introduced trifluoromethanesulfonic acid at 40° C. Under a condition that the inside of the reactor was stirred, 180.0 kg of diphosphorus pentoxide powder of 98.5 wt % purity (molar ratio of trifluoromethanesulfonic acid to diphosphorus pentoxide was 1.9) was added. Then, temperature of the warm water flowing through the jacket was increased. To correspond to the second step, it was tried to conduct an operation in which, while the inside of the reactor was kneaded, the inside temperature of the reactor was increased to 90° C. to generate trifluoromethanesulfonic anhydride, and the inside of the reactor was sucked by using a vacuum pump connected to the reactor, thereby discharging the generated trifluoromethanesulfonic anhydride from the reactor. With this, viscosity of a glassy product generated in the inside became too high. Thus, even if a load of 45 kW as the maximum power of the kneader-type reactor used in the present test was given, the kneading became impossible. Therefore, the reaction was stopped.

Comparative Example 2

Using an apparatus similar to that of Example 1, the test was conducted. The kneader-type reactor was charged with 430.0 kg of trifluoromethanesulfonic acid of 99.5 wt % purity, followed by making warm water flow through the jacket to maintain the introduced trifluoromethanesulfonic acid at 40° C. Under a condition that the inside of the reactor was stirred, 180.0 kg of diphosphorus pentoxide powder of 98.5 wt % purity (molar ratio of trifluoromethanesulfonic acid to diphosphorus pentoxide was 2.3) was added. Then, temperature of the warm water flowing through the jacket was decreased. To correspond to the second step, it was tried to conduct an operation in which, while the inside of the reactor was kneaded, the inside temperature of the reactor was decreased to 25° C. to generate trifluoromethanesulfonic anhydride, and the inside of the reactor was sucked by using a vacuum pump connected to the reactor, thereby discharging the generated trifluoromethanesulfonic anhydride from the reactor. With this, a glassy material was generated in the inside. Due to its high viscosity, even if a load of 45 kW as the maximum power of the kneader-type reactor used in the present test was given, the kneading became impossible. Therefore, the reaction was stopped.

Comparative Example 3

Using an apparatus similar to that of Example 1, the test was conducted. The kneader-type reactor was charged with 430.0 kg of trifluoromethanesulfonic acid of 99.5 wt % purity, followed by making warm water flow through the jacket to maintain the introduced trifluoromethanesulfonic acid at 40° C. Under a condition that the inside of the reactor was stirred, 180.0 kg of diphosphorus pentoxide powder of 98.5 wt % purity (molar ratio of trifluoromethanesulfonic acid to diphosphorus pentoxide was 2.3) was added. Then, the heat medium flowing through the jacket was changed from warm water to steam. To correspond to the second step, while the inside of the reactor was kneaded by a power of 8 kW, the inside temperature of the reactor was increased to 110° C. to generate trifluoromethanesulfonic anhydride, and the inside of the reactor was sucked by using a vacuum pump connected to the reactor to conduct an operation of discharging the generated trifluoromethanesulfonic anhydride from the reactor. The trifluoromethanesulfonic anhydride discharged from the reactor was subjected to a liquefaction condensation by cooling at 10° C. using a shell and tube type cooler installed in the middle of piping connecting the reactor with the vacuum pump. The liquefied trifluoromethanesulfonic anhydride was recovered in a product tank. The reaction was conducted until complete no recognition of evaporation and discharge from the reactor. After terminating the reaction, the steam temperature was raised, and, while kneading the residue in the reactor at a power of 10 kW, the inside temperature of the reactor was changed to 120° C. to conduct the third step for recovering the unreacted trifluoromethanesulfonic acid. It was, however, not possible to obtain the recovered product. The trifluoromethanesulfonic anhydride obtained by the second step was 340.3 kg in weight and 91.4 wt % in purity. Furthermore, the trifluoromethanesulfonic acid ester was 6.2 wt %.

As yield of trifluoromethanesulfonic anhydride was calculated based on the trifluoromethanesulfonic acid from which the recovered amount was subtracted, it was found to be a low yield of 77.3%.

Comparative Example 4

Using an apparatus similar to that of Example 1, the test was conducted. The kneader-type reactor was charged with 430.0 kg of trifluoromethanesulfonic acid of 99.5 wt % purity, followed by making warm water flow through the jacket to maintain the introduced trifluoromethanesulfonic acid at 40° C. Under a condition that the inside of the reactor was stirred, 180.0 kg of diphosphorus pentoxide powder of 98.5 wt % purity (molar ratio of trifluoromethanesulfonic acid to diphosphorus pentoxide was 2.3) was added. Then, temperature of the warm water flowing through the jacket was increased. To correspond to the second step, while the inside of the reactor was kneaded by a power of 8 kW, the inside temperature of the reactor was increased to 90° C. to generate trifluoromethanesulfonic anhydride, and the inside of the reactor was sucked by using a vacuum pump connected to the reactor to conduct an operation of discharging the generated trifluoromethanesulfonic anhydride from the reactor. The trifluoromethanesulfonic anhydride discharged from the reactor was subjected to a liquefaction condensation by cooling at 10° C. using a shell and tube type cooler installed in the middle of piping connecting the reactor with the vacuum pump. The liquefied trifluoromethanesulfonic anhydride was recovered in a product tank. The recovered trifluoromethanesulfonic anhydride was 302.2 kg in weight. As purity of the recovered product was analyzed by using an NMR measurement apparatus (JNM-AL400, made by JEOL), purity was 97.5 wt %.

Then, the heat medium made to flow through the jacket of the kneader-type reactor was changed from warm water to steam, and there was conducted an operation for discharging the unreacted trifluoromethanesulfonic acid from the reactor, which corresponded to the third step, by increasing the inside temperature of the reactor until 150° C. and by sucking the inside of the reactor using a vacuum pump connected to the reactor, while kneading the residue of the reactor at a power of 10 kW. The unreacted trifluoromethanesulfonic acid discharged from the reactor was subjected to a liquefaction condensation by cooling to 10° C. using a shell and tube type cooler installed in the middle of the piping connecting the reactor with the vacuum pump. The liquefied trifluoromethanesulfonic acid was recovered in a tank for recovering the unreacted trifluoromethanesulfonic acid. The recovered trifluoromethanesulfonic acid was 91.2 kg in weight. As composition of the recovered product was analyzed by using an NMR measurement apparatus (JNM-AL400, made by JEOL), purity of trifluoromethanesulfonic acid was 58.2 wt %, trifluoromethanesulfonic anhydride was 16.6 wt %, and the trifluoromethanesulfonic acid ester was 25.2 wt %.

As yield of trifluoromethanesulfonic anhydride was calculated based on the trifluoromethanesulfonic acid from which the recovered unreacted trifluoromethanesulfonic acid was subtracted, it was found to be 83.6%, which was a yield lower than 85.0%.

Comparative Example 5

Using an apparatus similar to that of Example 1, the test was conducted. The kneader-type reactor was charged with 430.0 kg of trifluoromethanesulfonic acid of 99.5 wt % purity, followed by making warm water flow through the jacket to maintain the introduced trifluoromethanesulfonic acid at 40° C. Under a condition that the inside of the reactor was stirred, 180.0 kg of diphosphorus pentoxide powder of 98.5 wt % purity (molar ratio of trifluoromethanesulfonic acid to diphosphorus pentoxide was 2.3) was added. Then, temperature of the warm water flowing through the jacket was changed. To correspond to the second step, while the inside of the reactor was kneaded by a power of 8 kW, the inside temperature of the kneader-type reactor was increased to 45° C. to generate trifluoromethanesulfonic anhydride, and the inside of the reactor was sucked by using a vacuum pump connected to the reactor to conduct an operation of discharging the generated trifluoromethanesulfonic anhydride from the reactor. The trifluoromethanesulfonic anhydride discharged from the reactor was subjected to a liquefaction condensation by cooling at 10° C. using a shell and tube type cooler installed in the middle of piping connecting the reactor with the vacuum pump. The liquefied trifluoromethanesulfonic anhydride was recovered in a product tank. The recovered trifluoromethanesulfonic anhydride was 289.5 kg in weight. As purity of the recovered product was analyzed by using an NMR measurement apparatus (JNM-AL400, made by JEOL), purity was 98.3 wt %.

Then, the temperature of warm water flowing through the jacket of the kneader-type reactor was changed, and there was conducted an operation for discharging the unreacted trifluoromethanesulfonic acid from the reactor, which corresponded to the third step, by increasing the inside temperature of the reactor until 90° C. and by sucking the inside of the reactor using a vacuum pump connected to the reactor, while kneading the residue of the reactor at a power of 10 kW. The unreacted trifluoromethanesulfonic acid discharged from the reactor was subjected to a liquefaction condensation by cooling to 10° C. using a shell and tube type cooler installed in the middle of the piping connecting the reactor with the vacuum pump. The liquefied trifluoromethanesulfonic acid was recovered in a tank for recovering the unreacted trifluoromethanesulfonic acid. The recovered trifluoromethanesulfonic acid was 48.2 kg in weight, and purity was 53.6 wt %. Trifluoromethanesulfonic anhydride was 45.8 wt %, and the trifluoromethanesulfonic acid ester was 0.6 wt %.

As yield of trifluoromethanesulfonic anhydride was calculated based on trifluoromethanesulfonic acid from which the recovered, unreacted trifluoromethanesulfonic acid was subtracted, it was found to be a low yield of 75.3%.

The results of Examples 1-9 and Comparative Examples 1-5 are shown in Table 1. Yield of each example was not lower than 90%.

TABLE 1

| No. | 1st step Molar ratio (TMS/P$_2$O$_5$) | 1st step Introduction order | 1st step Temp. at introduction (° C.) | 2nd step Reaction temp. (° C.) | 3rd step Unreacted substance evaporation temp. (° C.) | Yield (%) |
|---|---|---|---|---|---|---|
| Ex. 1 | 2.3 | TMS→P$_2$O$_5$ | 40 | 90 | 120 | 96.1 |
| Ex. 2 | 2.1 | TMS→P$_2$O$_5$ | 40 | 90 | 120 | 95.8 |
| Ex. 3 | 2.9 | TMS→P$_2$O$_5$ | 40 | 90 | 120 | 92.4 |
| Ex. 4 | 2.3 | TMS→P$_2$O$_5$ | 40 | 45 | 120 | 94.9 |
| Ex. 5 | 2.3 | TMS→P$_2$O$_5$ | 40 | 90 | 138 | 95.6 |
| Ex. 6 | 2.3 | Concurrent | 40 | 90 | 120 | 95.8 |
| Ex. 7 | 2.3 | P$_2$O$_5$→TMS | 40 | 90 | 120 | 92.9 |
| Ex. 8 | 2.3 | TMS→P$_2$O$_5$ | 80 | 90 | 120 | 95.6 |
| Ex. 9 | 2.3 | TMS→P$_2$O$_5$ | 25 | 90 | 120 | 92.9 |
| Com. Ex. 1 | 1.9 | TMS→P$_2$O$_5$ | 40 | 90 | Kneading impossible | — |
| Com. Ex. 2 | 2.3 | TMS→P$_2$O$_5$ | 40 | 25 | Kneading impossible | — |
| Com. Ex. 3 | 2.3 | TMS→P$_2$O$_5$ | 40 | 110 | 120 | 77.3 |
| Com. Ex. 4 | 2.3 | TMS→P$_2$O$_5$ | 40 | 90 | 150 | 83.6 |
| Com. Ex. 5 | 2.3 | TMS→P$_2$O$_5$ | 40 | 45 | 90 | 75.3 |

TMS refers to trifluoromethanesulfonic acid.

INDUSTRIAL USABILITY

It is possible to obtain a fluoroalkanesulfonic anhydride with high yield by the production method of the present invention. Therefore, it is a more efficient production method, as compared with conventional processes for producing fluoroalkanesulfonic acids, and can be provided as an industrial production method.

The invention claimed is:

1. A method for producing trifluoromethanesulfonic anhydride by introducing trifluoromethanesulfonic acid and diphosphorus pentoxide into a kneader-type reactor having a maximum power of 1.0 kW or greater per an actual capacity of 100 L and equipped with at least two-shaft blades and by kneading them in the reactor by a power of 0.5 kW or greater per an actual capacity of 100 L, the method comprising:
   a first step of introducing the trifluoromethanesulfonic acid and diphosphorus pentoxide into the reactor such that a molar ratio of a total amount of the trifluoromethanesulfonic acid introduced to a total amount of the diphosphorus pentoxide introduced becomes 2.0 or greater and less than 3.0,
   wherein a liquid temperature of the trifluoromethanesulfonic acid is 30° C. or higher and lower than 100° C. when introducing diphosphorus pentoxide into the reactor in the first step;
   a second step in which the trifluoromethanesulfonic acid is reacted with the diphosphorus pentoxide, while kneading the trifluoromethanesulfonic acid and the diphosphorus pentoxide, which have been introduced in the first step, at a temperature in the reactor that is 40° C. or higher and is lower than 100° C., to produce the trifluoromethanesulfonic anhydride as a main product and metaphosphoric acid as a by-product, in which the trifluoromethanesulfonic anhydride as the main product is discharged from the reactor, and in which the trifluoromethanesulfonic anhydride, which has been discharged by the second step, is liquefied and recovered by cooling; and
   a third step of discharging the unreacted trifluoromethanesulfonic acid from the reactor, while further kneading a residue in the reactor, which is obtained by the second step, at a temperature in the reactor that is 100° C. or higher and is lower than 140° C.,
   wherein the method is characterized by that the unreacted trifluoromethanesulfonic acid, which is discharged by the third step, is used as a total or part of the trifluoromethanesulfonic acid introduced in the first step.

2. The method for producing the trifluoromethanesulfonic anhydride as claimed in claim 1, wherein, in the first step, in terms of the order of introducing the trifluoromethanesulfonic acid and diphosphorus pentoxide, the trifluoromethanesulfonic acid and then diphosphorus pentoxide are introduced, or the trifluoromethanesulfonic acid and diphosphorus pentoxide are introduced simultaneously.

3. The method for producing the trifluoromethanesulfonic anhydride as claimed in claim 1, comprising:
   a fourth step of adding orthophosphoric acid to a residue in the reactor, which is obtained by the third step, to conduct a reaction with the metaphosphoric acid, thereby synthesizing pyrophosphoric acid; and
   a fifth step of discharging a residue containing the pyrophosphoric acid, which has been synthesized by the fourth step, from the reactor.

4. The method for producing the trifluoromethanesulfonic anhydride as claimed in claim 3, wherein water is added to a residue discharged by the fifth step to conduct a reaction with the pyrophosphoric acid in the residue, thereby synthesizing orthophosphoric acid, and that the obtained orthophosphoric acid is used as a total or part of the orthophosphoric acid added by the fourth step.

5. The method for producing the trifluoromethanesulfonic anhydride as claimed in claim 1, wherein the kneader-type reactor has a maximum power of 2.0 kW or greater per an actual capacity of 100 L.

6. The method for producing the trifluoromethanesulfonic anhydride as claimed in claim 1, wherein, in the second step, the trifluoromethanesulfonic anhydride, which has been discharged by the second step, is liquefied and recovered by cooling at a temperature of 10° C. or lower.

7. The method for producing the trifluoromethanesulfonic anhydride as claimed in claim 1, wherein the unreacted trifluoromethanesulfonic acid, which has been discharged by the third step, is liquefied and recovered by cooling.

8. The method for producing the trifluoromethanesulfonic anhydride as claimed in claim 7, wherein the unreacted trifluoromethanesulfonic acid is liquefied and recovered by cooling at a temperature of 10° C. or lower.

9. A method for producing trifluoromethanesulfonic anhydride by introducing a trifluoromethanesulfonic acid and diphosphorus pentoxide into a kneader-type reactor having a maximum power of 1.0 kW or greater per an actual capacity of 100 L and equipped with at least two-shaft blades and by kneading them in the reactor by a power of 0.5 kW or greater per an actual capacity of 100 L, the method comprising:

a first step of introducing the trifluoromethanesulfonic acid and diphosphorus pentoxide into the reactor such that a molar ratio of a total amount of the trifluoromethanesulfonic acid introduced to a total amount of the diphosphorus pentoxide introduced becomes 2.0 or greater and less than 2.5, wherein, in the first step, in terms of the order of introducing the trifluoromethanesulfonic acid and diphosphorus pentoxide, the trifluoromethanesulfonic acid and then diphosphorus pentoxide are introduced, or the trifluoromethanesulfonic acid and diphosphorus pentoxide are introduced simultaneously, wherein, in the first step, when introducing diphosphorus pentoxide into the reactor, a liquid temperature of the trifluoromethanesulfonic acid is 30° C. or higher and lower than 100° C.;

a second step in which the trifluoromethanesulfonic acid is reacted with the diphosphorus pentoxide, while kneading the trifluoromethanesulfonic acid and the diphosphorus pentoxide, which have been introduced in the first step, at a temperature in the reactor that is 40° C. or higher and is lower than 100° C., to produce the trifluoromethanesulfonic anhydride as a main product and metaphosphoric acid as a by-product, and in which the trifluoromethanesulfonic anhydride as the main product is discharged from the reactor, wherein, the trifluoromethanesulfonic anhydride, which discharged by the second step, is liquefied and recovered by cooling;

a third step of discharging the unreacted trifluoromethanesulfonic acid from the reactor, while further kneading a residue in the reactor, which is obtained by the second step, at a temperature in the reactor that is 100° C. or higher and is lower than 140° C., wherein the method is characterized by that the unreacted trifluoromethanesulfonic acid, which is discharged by the third step, is used as a total or part of the trifluoromethanesulfonic acid introduced in the first step;

a fourth step of adding orthophosphoric acid to a residue in the reactor, which is obtained by the third step, to conduct a reaction with the metaphosphoric acid, thereby synthesizing pyrophosphoric acid; and a fifth step of discharging a residue containing the pyrophosphoric acid, which has been synthesized by the fourth step, from the reactor, wherein water is added to a residue discharged by the fifth step to conduct a reaction with the pyrophosphoric acid in the residue, thereby synthesizing orthophosphoric acid, and that the obtained orthophosphoric acid is used as a total or part of the orthophosphoric acid added by the fourth step.

10. The method for producing the trifluoromethanesulfonic anhydride as claimed in claim 9, wherein, in the second step, the trifluoromethanesulfonic anhydride, which has been discharged, is liquefied and recovered by cooling at a temperature of 10° C. or lower.

11. The method for producing the trifluoromethanesulfonic anhydride as claimed in claim 9, wherein the unreacted trifluoromethanesulfonic acid, which has been discharged by the third step, is liquefied and recovered by cooling.

12. The method for producing the trifluoromethanesulfonic anhydride as claimed in claim 11, wherein the unreacted trifluoromethanesulfonic acid is liquefied and recovered by cooling at a temperature of 10° C. or lower.

* * * * *